US009623135B2

(12) United States Patent
Joshi et al.

(10) Patent No.: US 9,623,135 B2
(45) Date of Patent: Apr. 18, 2017

(54) VOLATILE SUBSTANCE DELIVERY SYSTEM

(71) Applicant: Microlin, LLC, Salt Lake City, UT (US)

(72) Inventors: Ashok V Joshi, Salt Lake City, UT (US); David J Erekson, Tooele, UT (US); Jessica Elwell, Salt Lake City, UT (US); Jeremy Heiser, Salt Lake City, UT (US)

(73) Assignee: Microlin, LLC, Salt Lake City, UT (US)

( * ) Notice: Subject to any disclaimer, the term of this patent is extended or adjusted under 35 U.S.C. 154(b) by 157 days.

(21) Appl. No.: 14/537,691

(22) Filed: Nov. 10, 2014

(65) Prior Publication Data

US 2015/0130088 A1 May 14, 2015

Related U.S. Application Data

(60) Provisional application No. 61/902,031, filed on Nov. 8, 2013.

(51) Int. Cl.

*A61L 9/00* (2006.01)
*B01F 3/04* (2006.01)
*A61L 9/03* (2006.01)
*A61L 9/12* (2006.01)

(52) U.S. Cl.

CPC ............... *A61L 9/032* (2013.01); *A61L 9/122* (2013.01); *A61L 9/127* (2013.01); *B01F 3/04* (2013.01); *A61L 9/037* (2013.01)

(58) Field of Classification Search

CPC .. B01F 3/04; A61L 9/032; A61L 9/037; A61L 9/122; A61L 9/127
USPC ..................... 261/30, 142, DIG. 88, DIG. 89
See application file for complete search history.

(56) References Cited

U.S. PATENT DOCUMENTS 4,623,337 A 11/1986 Maurice
5,879,095 A 3/1999 Gueret
6,390,453 B1 * 5/2002 Frederickson ........ A61M 15/02 261/100
2005/0036823 A1 2/2005 Butcher et al.
2005/0185940 A1 8/2005 Joshi et al.
2006/0292304 A1 12/2006 Tisone

OTHER PUBLICATIONS

Copenheaver et al. "International Search Report" for PCT Application No. PCT/US2015/017837, mailed Jun. 3, 2015, 2 pages.
Copenheaver et al. "Written Opinion of the International Searching Authority" for PCT Application No. PCT/US2015/017837, mailed Jun. 3, 2015, 8 pages.

* cited by examiner

*Primary Examiner* — Robert A Hopkins
(74) *Attorney, Agent, or Firm* — Brian C. Trask

(57) ABSTRACT

A volatile substance delivery system includes a volatile substance container to contain a volatile substance, a volatile substance delivery structure, and a volatile substance drop delivery system to deliver a drop of the volatile substance to the volatile substance delivery structure for delivery to an ambient environment.

17 Claims, 14 Drawing Sheets

100
102
114
116
110
112
108
106
104

VOLATILE SUBSTANCE DELIVERY SYSTEM

CROSS-REFERENCE TO RELATED APPLICATIONS

This application claims the benefit of U.S. Provisional Application No. 61/902,031, filed on Nov. 8, 2013, which is incorporated by reference herein in its entirety.

BACKGROUND

Conventional fragrance delivery systems use wicking to transfer the fragrance from a reservoir to a point of release from the device. However, wicking systems are inherently subject to many environmental conditions. This impacts the ability of the fragrance delivery system to control the release of the fragrance into the ambient environment. Without the ability to control the release of the fragrance, top notes typically evaporate first, followed by middle notes and then base notes (based on different volatility levels). In this way, conventional wicking systems over time often fail to provide full fragrances with the full range of combined notes.

SUMMARY

Embodiments of a system are described. In one embodiment, the system is a volatile substance delivery system. An embodiment of the volatile substance delivery system includes a volatile substance container to contain a volatile substance, a volatile substance delivery structure, and a volatile substance drop delivery system to deliver a drop of the volatile substance to the volatile substance delivery structure for delivery to an ambient environment. Other embodiments of the system are also described.

Embodiments of a system are also described. In one embodiment, the system is a volatile substance delivery system. In one embodiment, the volatile substance delivery system includes a volatile substance container to contain a volatile substance, an emanator to receive a controlled volume of the volatile substance from the volatile substance container, and a pump to deliver the controlled volume of the volatile substance to the emanator for delivery to an ambient environment. Other embodiments of the system are also described.

Embodiments of a system are also described. In one embodiment, the volatile substance delivery system includes a volatile substance container to contain a volatile substance, a heater to receive a controlled volume of the volatile substance from the volatile substance container, and a pump to deliver the controlled volume of the volatile substance to the emanator for delivery to an ambient environment. Other embodiments of the system are also described.

Other aspects and advantages of embodiments of the present invention will become apparent from the following detailed description, taken in conjunction with the accompanying drawings, illustrated by way of example of the principles of the invention.

BRIEF DESCRIPTION OF THE DRAWINGS

Throughout the description, similar reference numbers may be used to identify similar elements.

DETAILED DESCRIPTION

Figure 1:
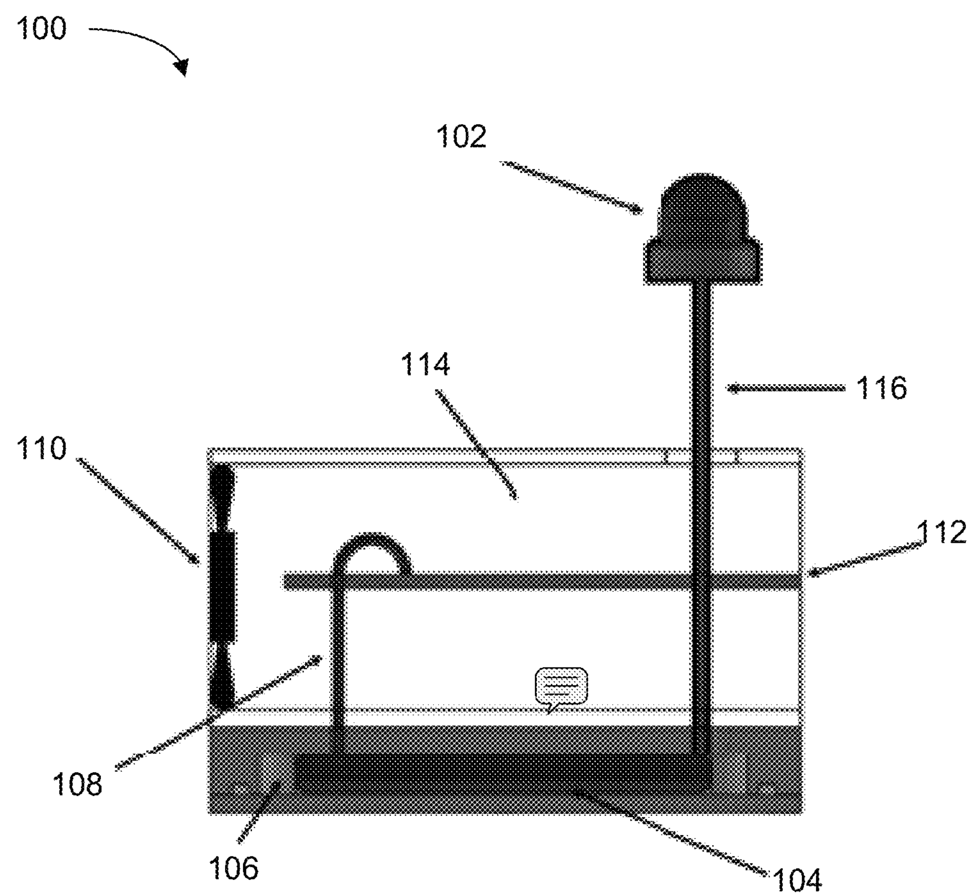
FIG. 1 illustrates one embodiment of a pressurized chamber fragrance delivery system.

It will be readily understood that the components of the embodiments as generally described herein and illustrated in the appended figures could be arranged and designed in a wide variety of different configurations. Thus, the following more detailed description of various embodiments, as represented in the figures, is not intended to limit the scope of the present disclosure, but is merely representative of various embodiments. While the various aspects of the embodiments are presented in drawings, the drawings are not necessarily drawn to scale unless specifically indicated.

The present invention may be embodied in other specific forms without departing from its spirit or essential characteristics. The described embodiments are to be considered in all respects only as illustrative and not restrictive. The scope of the invention is, therefore, indicated by the appended claims rather than by this detailed description. All changes which come within the meaning and range of equivalency of the claims are to be embraced within their scope.

Reference throughout this specification to features, advantages, or similar language does not imply that all of the features and advantages that may be realized with the present invention should be or are in any single embodiment of the invention. Rather, language referring to the features and advantages is understood to mean that a specific feature, advantage, or characteristic described in connection with an embodiment is included in at least one embodiment of the present invention. Thus, discussions of the features and advantages, and similar language, throughout this specification may, but do not necessarily, refer to the same embodiment.

Furthermore, the described features, advantages, and characteristics of the invention may be combined in any suitable manner in one or more embodiments. One skilled in the relevant art will recognize, in light of the description herein, that the invention can be practiced without one or more of the specific features or advantages of a particular embodiment. In other instances, additional features and advantages may be recognized in certain embodiments that may not be present in all embodiments of the invention.

Reference throughout this specification to "one embodiment," "an embodiment," or similar language means that a particular feature, structure, or characteristic described in connection with the indicated embodiment is included in at least one embodiment of the present invention. Thus, the phrases "in one embodiment," "in an embodiment," and similar language throughout this specification may, but do not necessarily, all refer to the same embodiment.

While many embodiments are described herein, at least some of the described embodiments facilitate on-demand delivery of a volatile substance. In general, the volatile substance refers to any fluid which is volatile such that it diffuses, evaporates, or otherwise changes in characteristics over time in certain environments. In some embodiments, the volatile substance may be a fragrance. Other embodiments may utilize other types of volatile substances. References to embodiments which utilize a fragrance are set forth as examples, but are not limiting to embodiments of the delivery system, which may deliver any of a variety of volatile substances.

The on-demand delivery of a fragrance may be used to create an expected ambiance or environment for a user. For example, a user may utilize fragrance to optimize the user's sleeping environment and to enhance the user's bedtime routine. Examples of other activities that may benefit from the use of fragrances include, but are not limited to, sleeping, studying, working, eating, and watching television.

In contrast to conventional wicking systems, embodiments described herein implement drop delivery systems. Drop delivery systems may be controlled more easily than conventional systems. Also, drop delivery systems can maintain full or broader range of notes over a longer period of time, if the fragrance is not subjected to evaporation or other degrading environmental conditions. This allows each drop of the fragrance to deliver a mix of top, middle, and base notes throughout the operating lifecycle of a fragrance volume within a fragrance delivery system.

Embodiments of a fragrance delivery system incorporate a fragrance reservoir and one of several possible structures and arrangements to deliver a specified amount of fragrance into the ambient environment. In some embodiments, the fragrance delivery system may include a combination of one or more of the following components: a fragrance reservoir, a pump system, an emanator, a fan, a heat source for heating air, a heat source for heating the fragrance, a housing, and an audio system. Other embodiments may include additional components.

A primary advantage of some embodiments described herein includes the ability to deliver the full depth of the fragrance, as opposed to just the high notes. In some embodiments, the system provides an immediate volume of fragrance that is then distributed into the ambient environment, to optimize an environment for a given activity. The volume of fragrance delivered is not subject to environmental conditions.

FIG. 1 illustrates one embodiment of a pressurized chamber fragrance delivery system 100. The illustrated pressurized chamber fragrance delivery system 100 includes a manual pump 102, a fragrance bag 104, an air chamber 106, a fragrance exit channel 108, a fan 110, an emanator 112, an air channel 114, and an air tube 116. Although the illustrated pressurized chamber fragrance delivery system 100 includes certain components to achieve specific functionality, other embodiments of the pressurized chamber fragrance delivery system 100 may include fewer or more components to achieve similar or different functionality.

In one embodiment, the manual pump 102 is used to pressurize the air chamber 106 containing the flexible fragrance bag 104. In one embodiment, the manual pump 102 is a manual air pump. Other embodiments may use other types of pumps. Pressurizing the air chamber 106 compresses the fragrance bag 104 to expel fragrance from the fragrance bag 104 through the fragrance exit channel 108 to the emanator 112. Some examples of emanator materials include, but are not limited to, porous polymers, simple cellular papers or films. In general, embodiments of the emanator 112 have a balance of absorption, wicking, and emanation properties that allow the emanator 112 to collect, distribute, and release the fragrance over time. The fan 110 moves air over the emanator 112 to deliver the fragrance into the ambient environment.

In some embodiments, the emanator 112 includes a porous material to collect, wick, and release the fragrance. The emanator 112 may or may not have its own structural integrity to maintain a specific shape while mounted within the fragrance delivery system. In some embodiments, the emanator material is applied to, or supported by, another support structure such as a cage or frame made of any suitable material.

Figure 2:
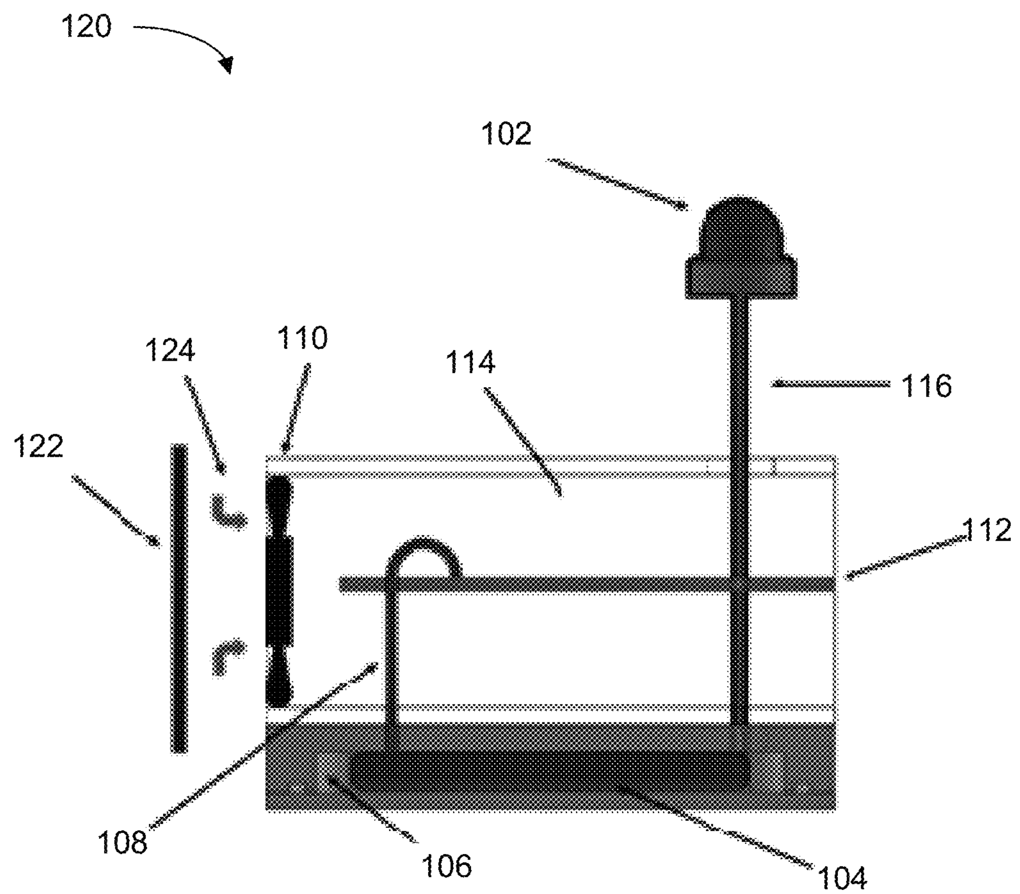
FIG. 2 illustrates another embodiment of a pressurized chamber fragrance delivery system which includes a heater.

FIG. 2 illustrates another embodiment of a pressurized chamber fragrance delivery system 120 which includes a heater 122. The illustrated heater 118 is located at or near the fan 110 to produce heated air 120 to be forced over the emanator 112. In this way, the heater 118 raises the temperature of the ambient air before it is moved over the emanator 112 by the fan 110. In some embodiments, heated air enhances the delivery of the fragrance into the ambient environment.

In other embodiments, the airflow may be conditioned (e.g., heated, cooled, humidified, dehumidified, etc.) in other ways to maintain the temperature at the emanator 112 at a specific temperature, or within a temperature range. In some embodiments, because of the controlled release available within a drop delivery system, the fragrance may be emitted within any ambient temperature ranging from freezing to boiling of the fragrance. In other embodiments, the airflow may be conditioned (e.g., humidified, dehumidified, etc.) in other ways to maintain other operating parameters at the emanator 112.

Figure 3:
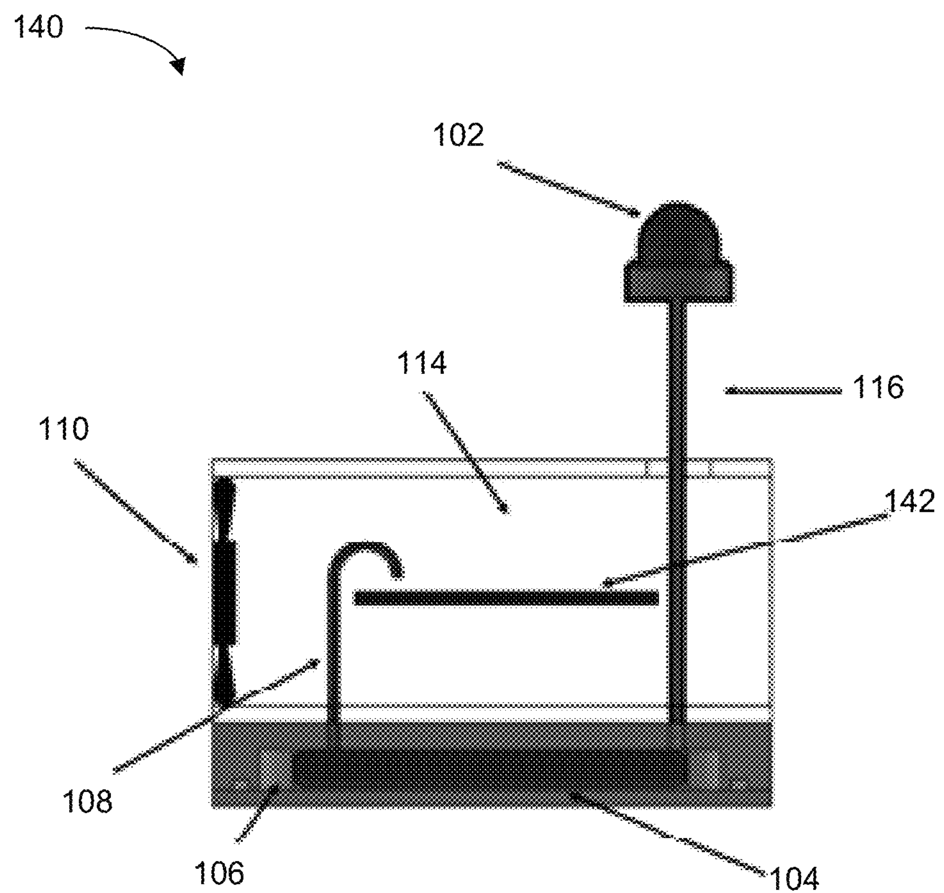
FIG. 3 illustrates another embodiment of a pressurized chamber fragrance delivery system which includes a heater instead of an emanator.

FIG. 3 illustrates another embodiment of a pressurized chamber fragrance delivery system 140 which includes a heater 142 instead of an emanator. The heater 142 may be any type of heater that is inert to the fragrance. Some examples of heaters include, but are not limited to, conductive rubber heaters, composite rubber and metal heaters, ceramic, and so forth. The heater 142 is located to receive fragrance from the fragrance exit channel 108 when the manual pump is activated. When the fragrance contacts the heater 142, the heater raises the temperature of the fragrance to promote evaporation. The airflow from the fan 110 moves over the heated fragrance to deliver the fragrance into the ambient environment.

In an alternative embodiment, an emanator may include, or be adjacent to a heater or heating element to heat up the fragrance. Some embodiments may include multiple heaters or heating elements, which may be located at different locations within a pressurized chamber fragrance delivery system.

Figure 4:
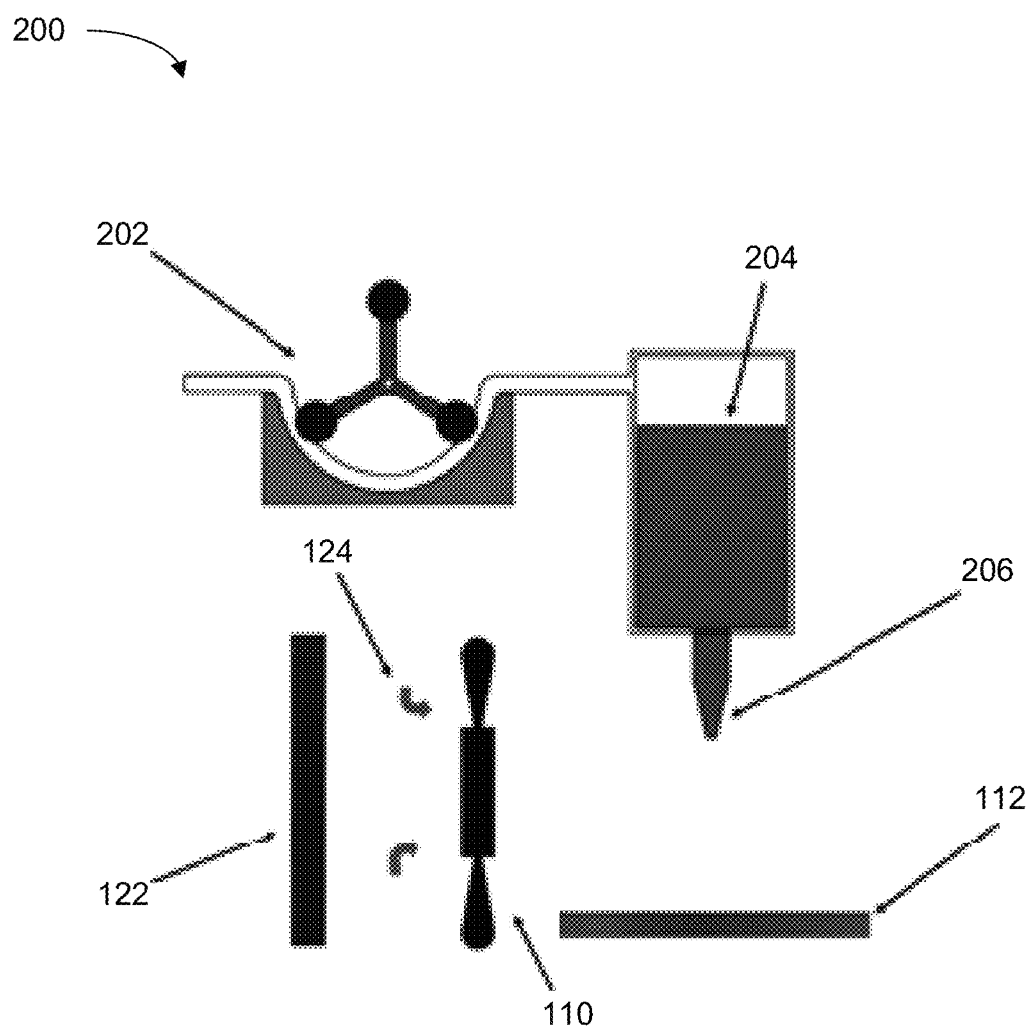
FIG. 4 illustrates another embodiment of a pressurized chamber fragrance delivery system which includes a peristaltic pump.

FIG. 4 illustrates another embodiment of a pressurized chamber fragrance delivery system 200 which includes a peristaltic pump 202. The peristaltic pump 202 operates to pump air into a fragrance chamber 204, which causes fragrance within the chamber to be emitted at an exit port 206. The emitted fragrance is absorbed into an emanator 112. A fan 110 is situated to force air across the emanator 112 and blow fragrance into the ambient environment.

In some embodiments, a heater 122 is disposed at or near the fan 110 to condition the air before it is moved by the fan 110. In some situations, heating the air might enhance delivery of the fragrance into the ambient environment.

Figure 5:
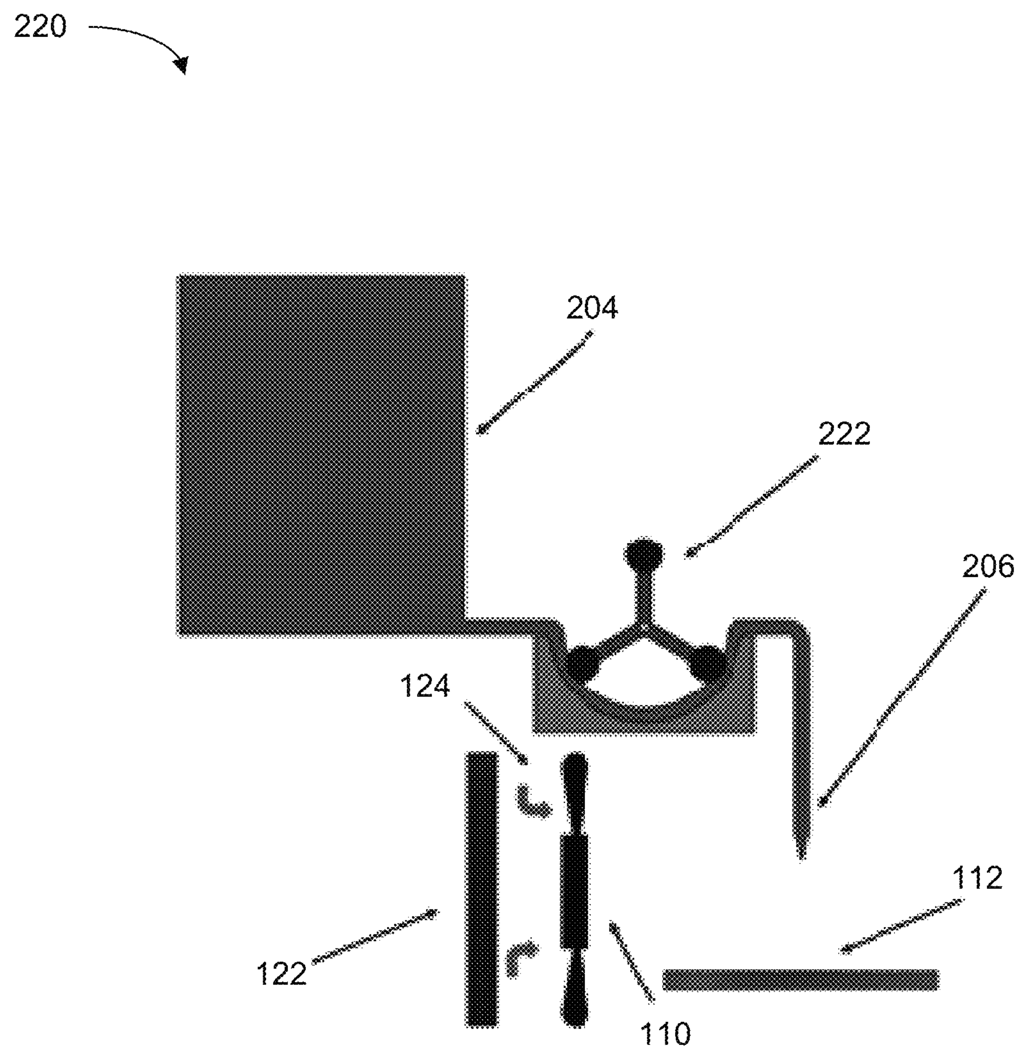
FIG. 5 illustrates another embodiment of a pressurized chamber fragrance delivery system which includes a peristaltic pump.

FIG. 5 illustrates another embodiment of a pressurized chamber fragrance delivery system 200 which includes a peristaltic pump 222. In this embodiment, the peristaltic pump 222 functions to pump fragrance from the fragrance chamber 204 to the exit port 206. Similar to the embodiment of FIG. 4, this embodiment results in emission of the fragrance to the emanator 112 for dispersion into the ambient environment.

Figure 6:
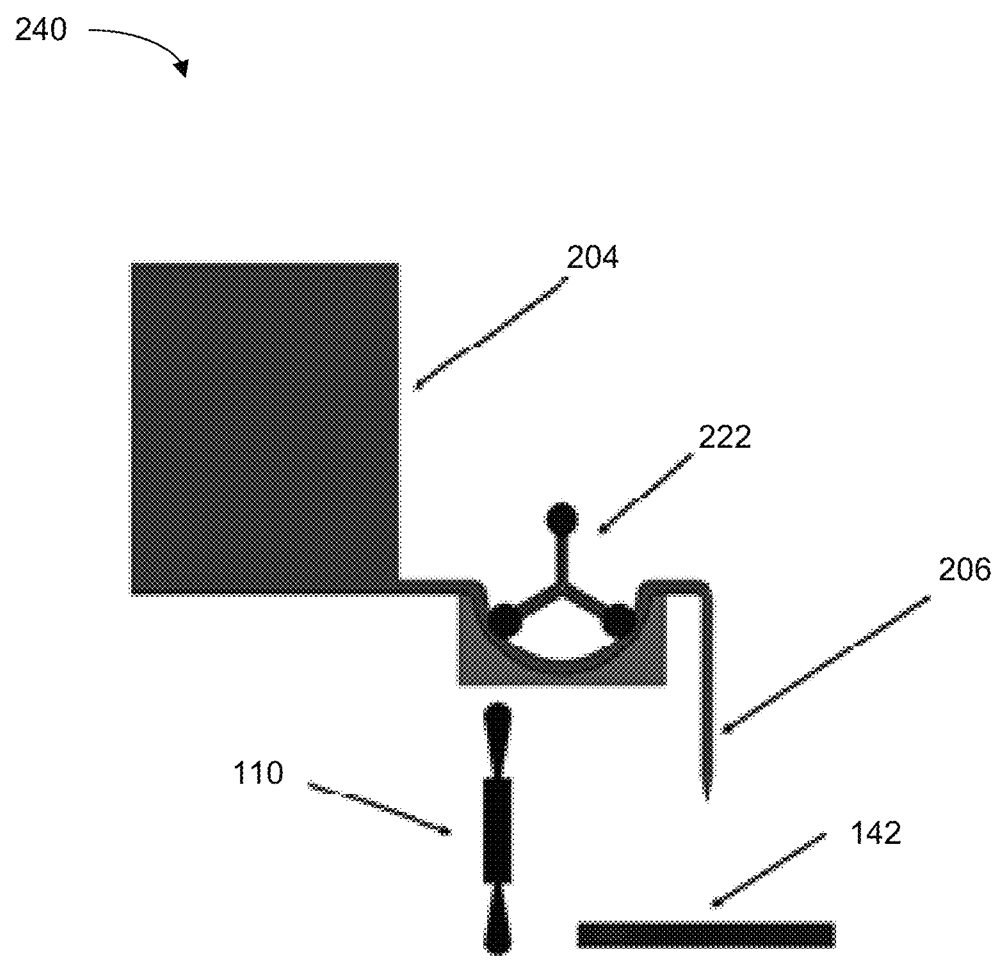
FIG. 6 illustrates another embodiment of a pressurized chamber fragrance delivery system which includes a peristaltic pump.

FIG. 6 illustrates another embodiment of a pressurized chamber fragrance delivery system 200 which includes a peristaltic pump 222. Similar to the embodiment of FIG. 3, the illustrated embodiment includes a heater 142 instead of an emanator. The heater 142 is located to receive fragrance from the exit port 206 when the peristaltic pump 222 is activated. When the fragrance contacts the heater 142, the heater 142 raises the temperature of the fragrance to promote evaporation. The airflow from the fan 110 moves over the heated fragrance to deliver the fragrance into the ambient environment.

Figure 7:
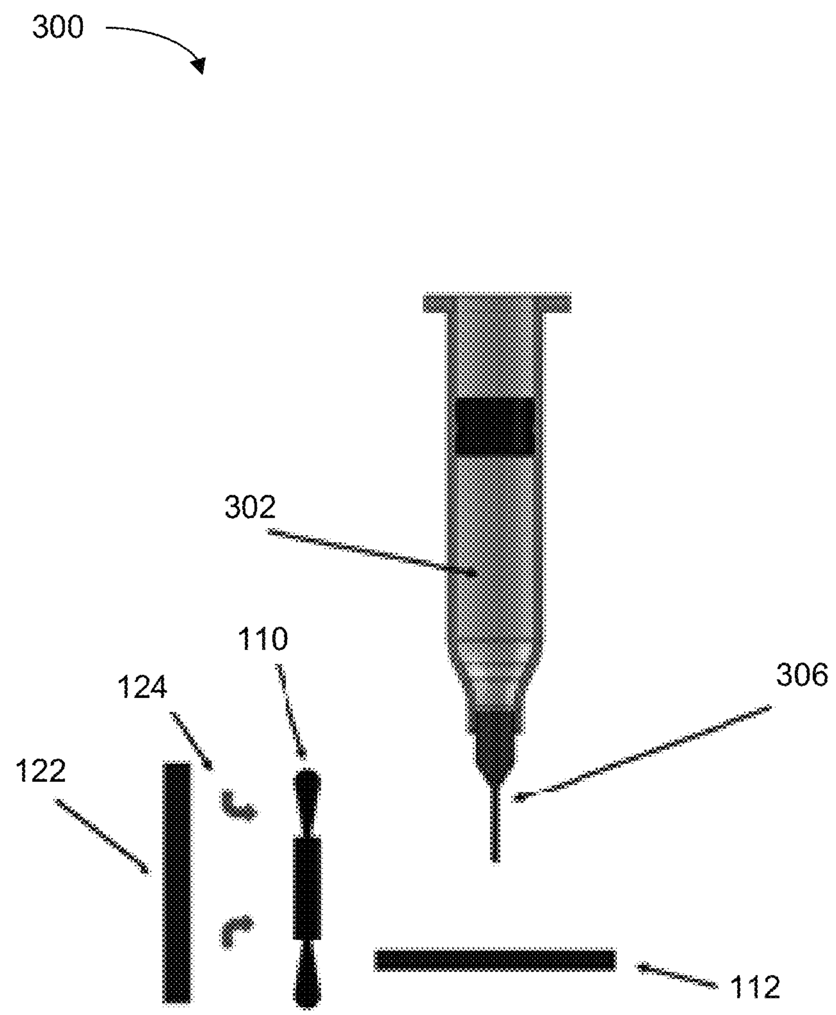
FIG. 7 illustrates another embodiment of a pressurized chamber fragrance delivery system which includes a cylindrical pump.

FIG. 7 illustrates another embodiment of a pressurized chamber fragrance delivery system 300 which includes a cylindrical pump 302. In one embodiment, the cylindrical pump 302 is a syringe style pump to deliver fragrance from an exit port 306 onto an emanator 112. A heater 122 raises the temperature of the ambient air 124 before it is moved over the emanator 112 by the fan 110. The heated air enhances the delivery the fragrance into the ambient environment.

Figure 8:
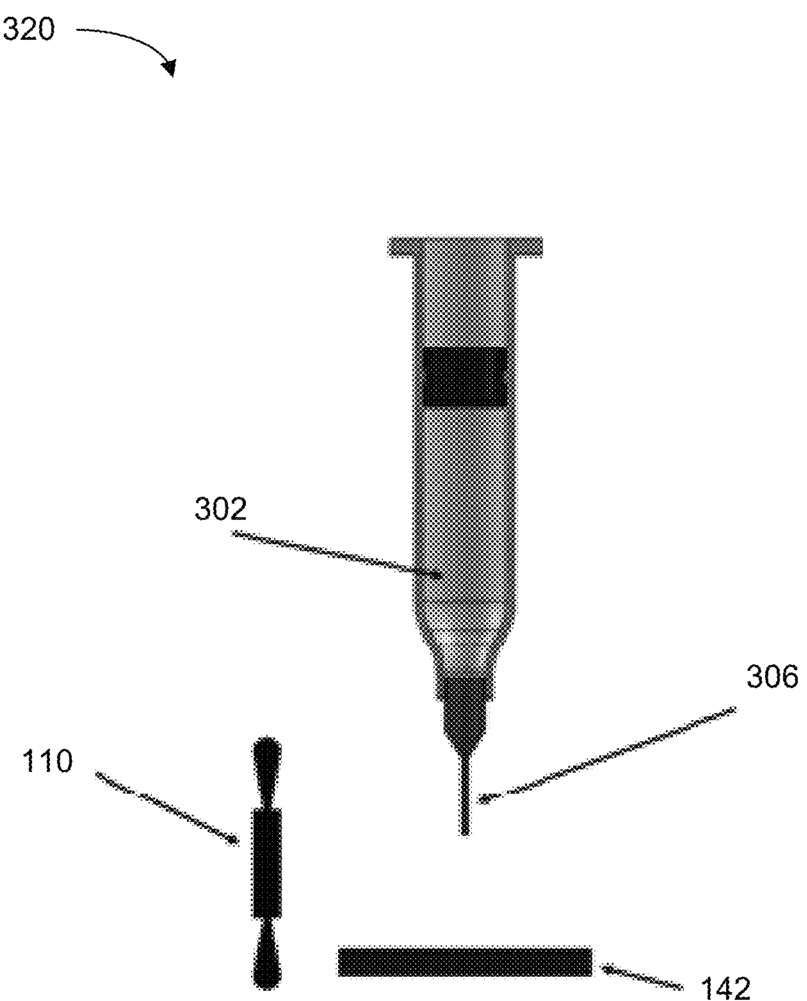
FIG. 8 illustrates another embodiment of a pressurized chamber fragrance delivery system which includes a cylindrical pump.

FIG. 8 illustrates another embodiment of a pressurized chamber fragrance delivery system 320 which includes a cylindrical pump 302. Similar to the embodiment of FIG. 3, the illustrated embodiment includes a heater 142 instead of an emanator. The heater 142 is located to receive fragrance from the exit port 306 when the cylindrical pump 302 is activated. When the fragrance contacts the heater 142, the heater 142 raises the temperature of the fragrance to promote evaporation. The airflow from the fan 110 moves over the heated fragrance to deliver the fragrance into the ambient environment.

Figure 9:
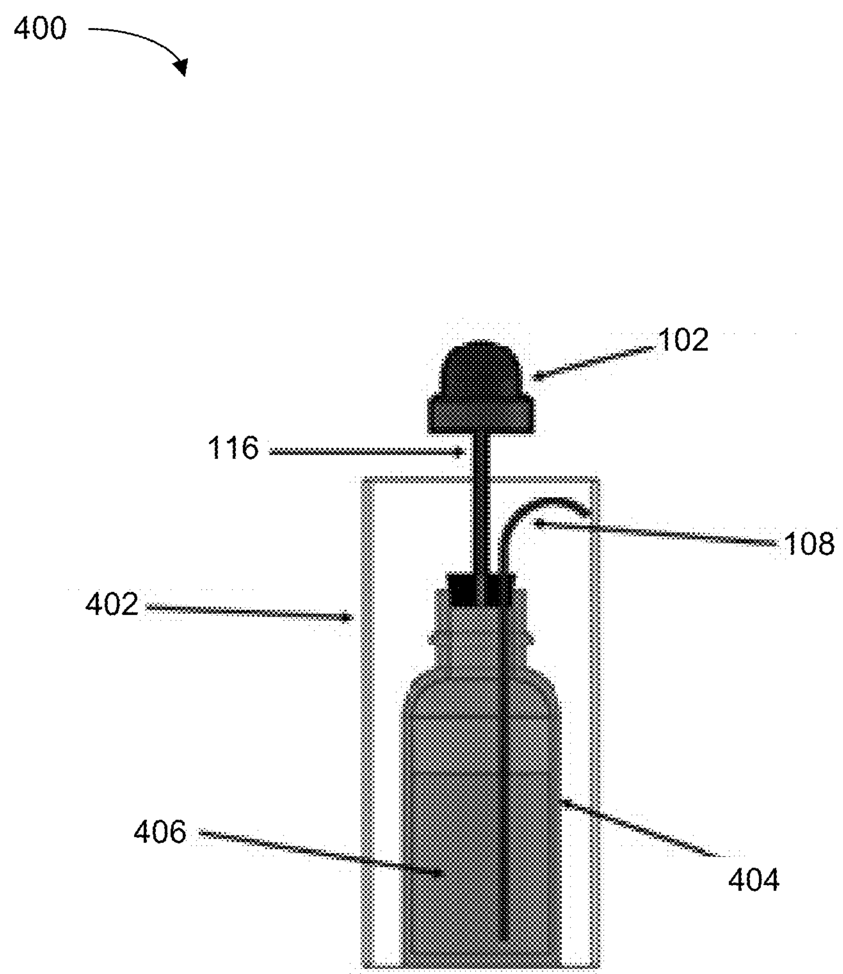
FIG. 9 illustrates another embodiment of a pressurized chamber fragrance delivery system which includes a cylindrical emanator surrounding the fragrance container.

FIG. 9 illustrates another embodiment of a pressurized chamber fragrance delivery system 400 which includes a cylindrical emanator 402 surrounding the fragrance container 404. The fragrance container 404, containing the fragrance 406, sits inside of a space or cavity at least partially defined by the emanator 402. In the depicted embodiment, the fragrance container 404 sits inside a cylindrical cage, although other embodiments may use any form of structure to enclose the fragrance container 404. A manual pump 102 (or other type of pump) can be used to force fragrance 406 from the fragrance container 404 through the fragrance exit channel 108 to the surrounding emanator 112.

Figure 10:
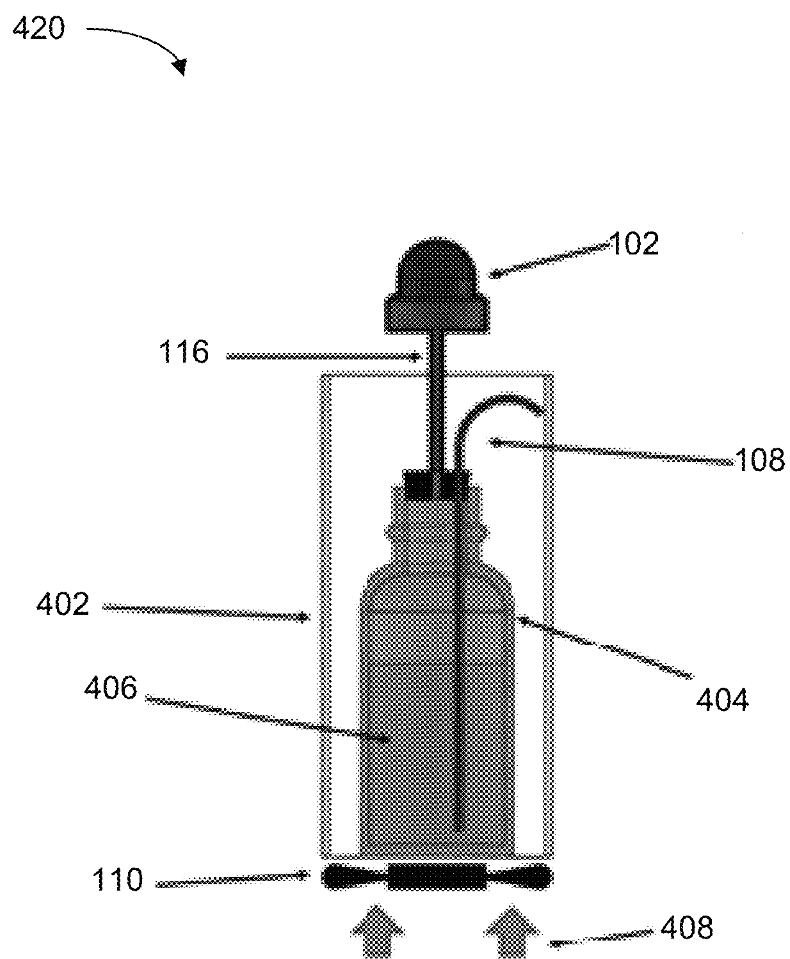
FIG. 10 illustrates another embodiment of a pressurized chamber fragrance delivery system.

FIG. 10 illustrates another embodiment of a pressurized chamber fragrance delivery system 420 which includes a cylindrical emanator 402 surrounding the fragrance container 404. The illustrated pressurized chamber fragrance delivery system 420 also includes a fan 110 to move ambient air 408 through the annular region between the fragrance container 404 and the cylindrical emanator 402. The fan 110 also may move the air 408 around the outside of the emanator 112.

Figure 11:
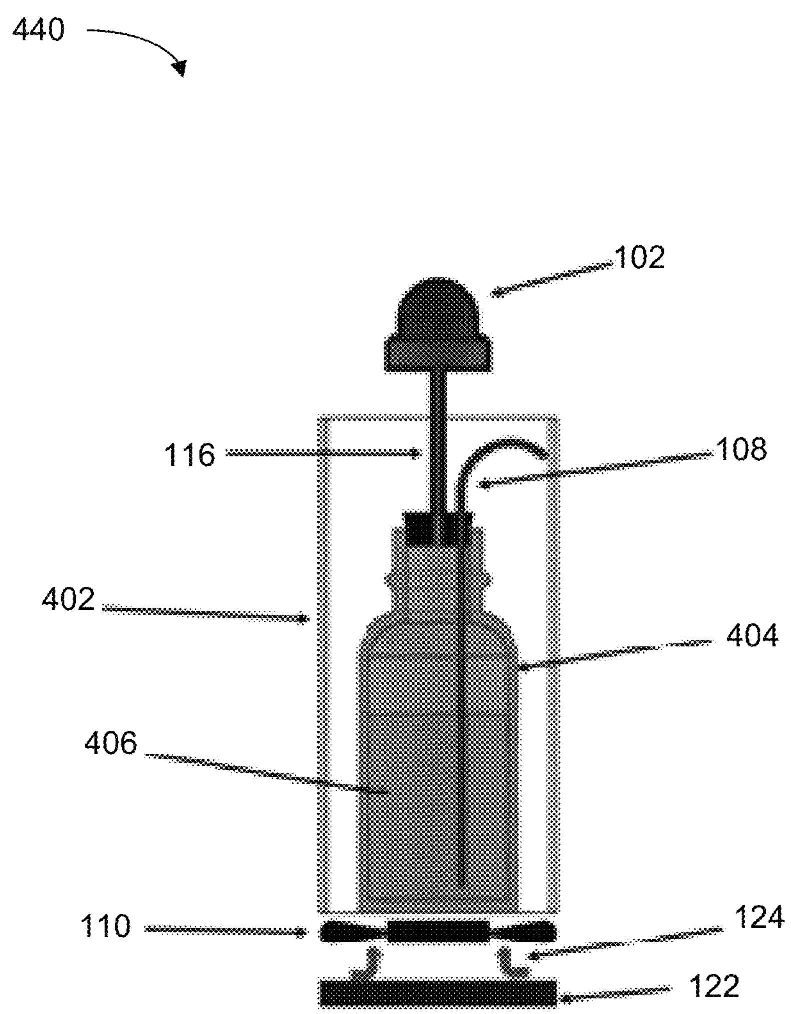
FIG. 11 illustrates another embodiment of a pressurized chamber fragrance delivery system which includes a cylindrical emanator surrounding the fragrance container.

FIG. 11 illustrates another embodiment of a pressurized chamber fragrance delivery system 440 which includes a cylindrical emanator 402 surrounding the fragrance container 404. A heater 122 raises the temperature of the ambient air 124 before it is moved over the emanator 112 by the fan 110. The heated air enhances the delivery the fragrance into the ambient environment.

Figure 12:
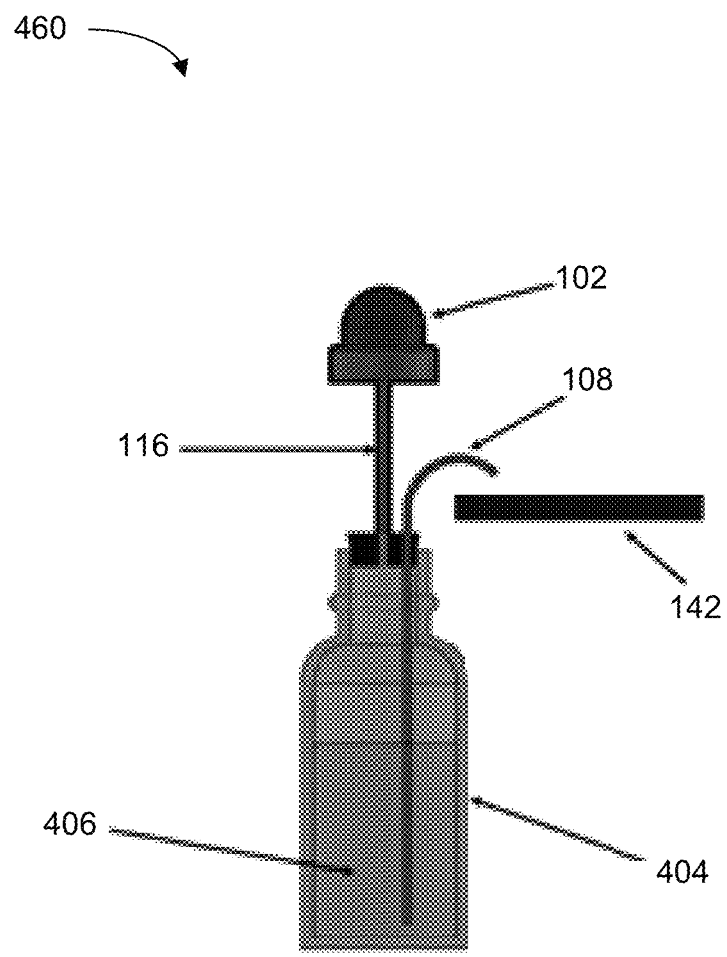
FIG. 12 illustrates another embodiment of a pressurized chamber fragrance delivery system which includes a cylindrical emanator surrounding the fragrance container.

FIG. 12 illustrates another embodiment of a pressurized chamber fragrance delivery system 460 which includes a cylindrical emanator 402 surrounding the fragrance container 404. Similar to the embodiment of FIG. 3, the illustrated embodiment includes a heater 142 instead of an emanator. The heater 142 is located to receive fragrance from the exit port 306 when the cylindrical pump 302 is activated. When the fragrance contacts the heater 142, the heater 142 raises the temperature of the fragrance to promote evaporation. The airflow from the fan 110 moves over the heated fragrance to deliver the fragrance into the ambient environment.

Figure 13:
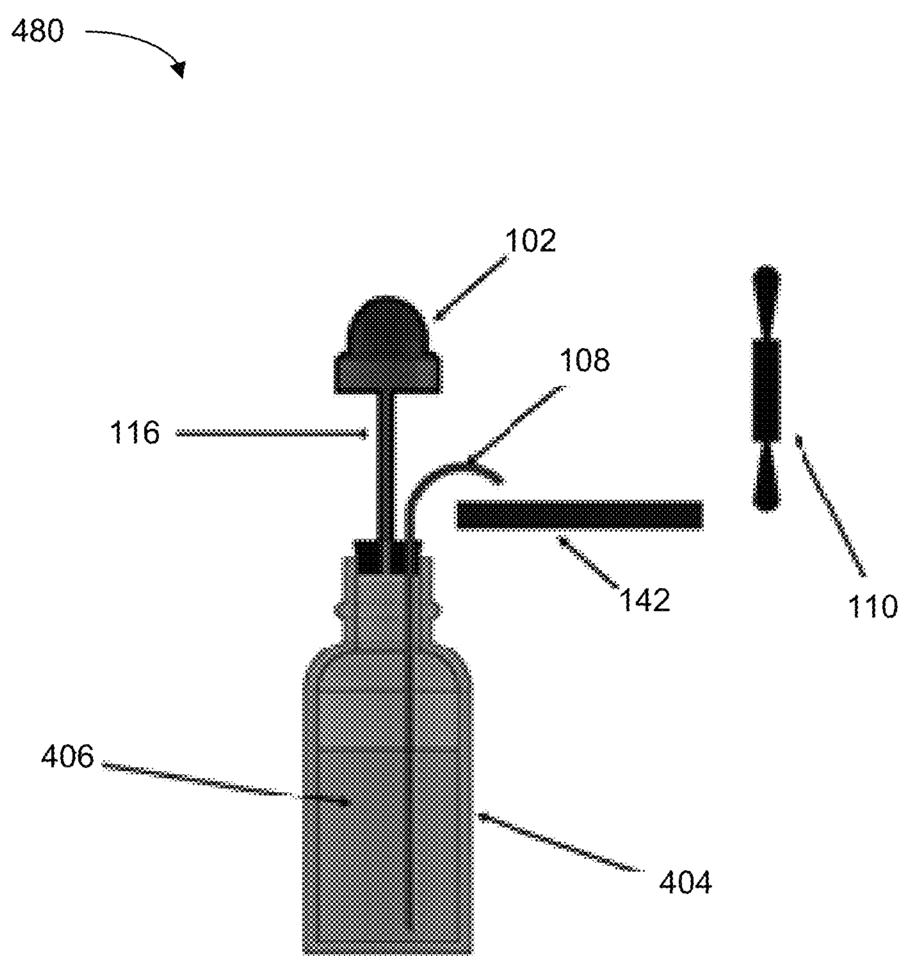
FIG. 13 illustrates another embodiment of a pressurized chamber fragrance delivery system which includes a cylindrical emanator surrounding the fragrance container.

FIG. 13 illustrates another embodiment of a pressurized chamber fragrance delivery system 480 which includes a cylindrical emanator 402 surrounding the fragrance container 404. The illustrated embodiment is similar to the embodiment shown in FIG. 13, with the addition of a fan 110 to apply airflow to the heater 142.

Figure 14:
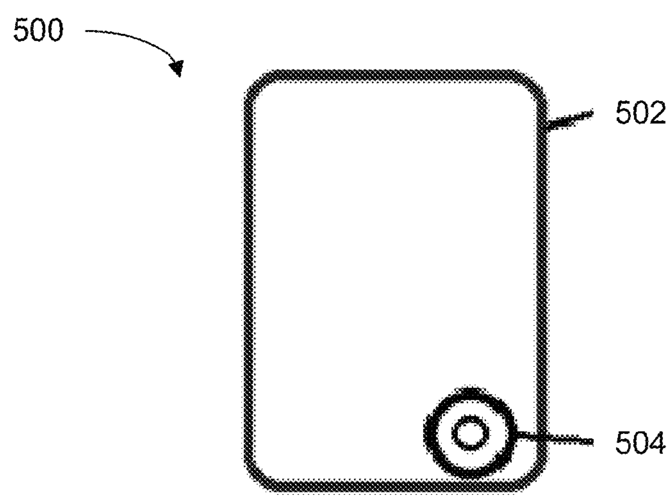
FIG. 14 illustrates one embodiment of a sound and scent system.

FIG. 14 illustrates one embodiment of a sound and scent system 500. In some embodiments, the sound and scent system 500 incorporates a fragrance delivery system 502 with a sound system 504 (e.g., audio speaker). The fragrance delivery system 502 can operate to deliver a specific scent into the ambient environment to promote a desired activity. The sound system 504 may incorporate one or more speakers to effectively deliver desired audio sounds. In further embodiments, the sound system 504 may incorporate one or more sensors to activate the fragrance delivery based on frequencies or other sound characteristics.

Figure 15:
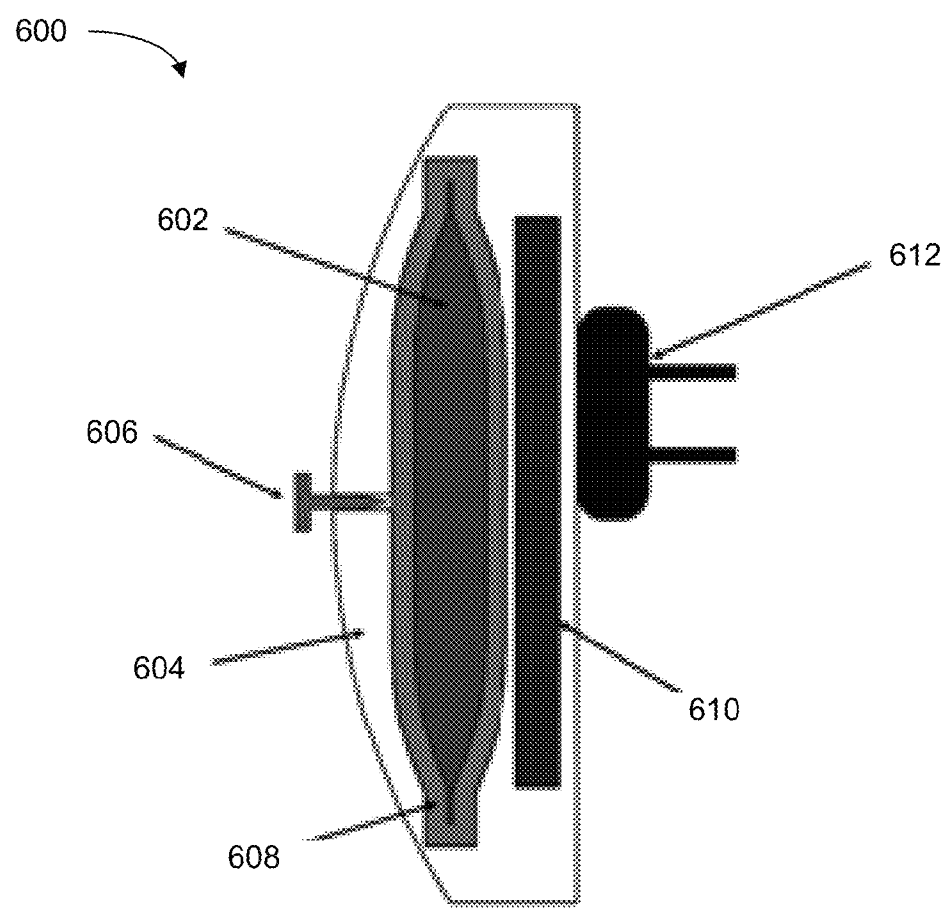
FIG. 15 illustrates one embodiment of a single dose fragrance delivery system.

FIG. 15 illustrates one embodiment of a single dose fragrance delivery system 600. In one embodiment, fragrance is disposed in a single dose bag 602 or other container. The single dose bag is placed within a pouch holder 604. A puncture tool 606 operates to puncture or pierce the single dose bag 602. By creating an opening in the single dose bag 602, the fragrance saturates an emanator 608 surrounding the single dose bag 602. In other embodiments, the emanator 608 at least partially surrounds the puncture point, but does not necessarily fully surround the single dose bag 602.

The pouch (with the single dose bag 602 and the emanator 608 may be placed next to a heating element 610. The heating element 610 may be powered by an electrical plug 612. The heating element 610 raises the temperature of the fragrance to promote evaporation. The single dose bag 602 may be replaceable and/or interchangeable to allow for repeated use and/or the delivery of a variety of fragrances.

In the above description, specific details of various embodiments are provided. However, some embodiments may be practiced with less than all of these specific details. In other instances, certain methods, procedures, components, structures, and/or functions are described in no more detail than to enable the various embodiments of the invention, for the sake of brevity and clarity.

Although the operations of the method(s) herein are shown and described in a particular order, the order of the operations of each method may be altered so that certain operations may be performed in an inverse order or so that certain operations may be performed, at least in part, concurrently with other operations. In another embodiment, instructions or sub-operations of distinct operations may be implemented in an intermittent and/or alternating manner.

Although specific embodiments of the invention have been described and illustrated, the invention is not to be limited to the specific forms or arrangements of parts so described and illustrated. The scope of the invention is to be defined by the claims appended hereto and their equivalents.

What is claimed is:

1. A volatile substance delivery system comprising:

a volatile substance container to contain a volatile substance;

a volatile substance delivery structure;

a volatile substance drop delivery system to deliver a drop of the volatile substance to the volatile substance delivery structure for delivery to an ambient environment; and a pump coupled to the volatile substance container to pump a volume of the volatile substance out of the volatile substance container, wherein the pump comprises a manual pump operable by manual interaction by a user.

2. The volatile substance delivery system of claim 1, wherein the pump comprises a cylindrical pump to deliver a controlled volume of the volatile substance from the volatile substance container.

3. The volatile substance delivery system of claim 1, wherein the volatile substance delivery structure comprises a heater to raise a temperature of the drop of the volatile substance.

4. The volatile substance delivery system of claim 3, wherein the heater is disposed to receive the drop of the volatile substance on a surface of the heater.

5. The volatile substance delivery system of claim 4, wherein the heater is disposed near a fan to heat air entering into or exiting from the fan toward the volatile substance delivery structure to receive the drop of the volatile substance on a surface of the heater.

6. The volatile substance delivery system of claim 1, further comprising a fan to generate airflow, wherein the airflow is directed toward the volatile substance delivery structure.

7. A volatile substance delivery system comprising:

a volatile substance container to contain a volatile substance;

a volatile substance delivery structure; and a volatile substance drop delivery system to deliver a drop of the volatile substance to the volatile substance delivery structure for delivery to an ambient environment, the volatile substance delivery structure comprising an emanator with absorption, wicking, and emanation properties, wherein the emanator surrounds at least a portion of the volatile substance container.

8. The volatile substance delivery system of claim 7, wherein the volatile substance delivery system further comprises a heater to generate heat and raise a temperature of the drop of the volatile substance within the volatile substance delivery system.

9. The volatile substance delivery system of claim 7, further comprising a fan to generate airflow, wherein the airflow is directed toward the volatile substance delivery structure.

10. The volatile substance delivery system of claim 7, wherein the volatile substance delivery structure comprises a heater to raise a temperature of the drop of the volatile substance.

11. The volatile substance delivery system of claim 10, wherein the heater is disposed to receive the drop of the volatile substance on a surface of the heater.

12. The volatile substance delivery system of claim 10, wherein the heater is disposed near a fan to heat air entering into or exiting from the fan toward the volatile substance delivery structure to receive the drop of the volatile substance on a surface of the heater.

13. A volatile substance delivery system comprising:

a volatile substance container to contain a volatile substance;

a volatile substance delivery structure;

a volatile substance drop delivery system to deliver a drop of the volatile substance to the volatile substance delivery structure for delivery to an ambient environment; and a pump coupled to the volatile substance container to pump a volume of the volatile substance out of the volatile substance container, the pump comprising a peristaltic pump to deliver a predefined volume of the volatile substance from the volatile substance container, wherein the peristaltic pump is disposed upstream of the volatile substance container to deliver fluid into the volatile substance container and force a corresponding volume of the volatile substance out of the volatile substance container.

14. The volatile substance delivery system of claim 13, wherein the volatile substance delivery structure comprises a heater to raise a temperature of the drop of the volatile substance.

15. The volatile substance delivery system of claim 14, wherein the heater is disposed to receive the drop of the volatile substance on a surface of the heater.

16. The volatile substance delivery system of claim 14, wherein the heater is disposed near a fan to heat air entering into or exiting from the fan toward the volatile substance delivery structure to receive the drop of the volatile substance on a surface of the heater.

17. The volatile substance delivery system of claim 13, further comprising a fan to generate airflow, wherein the airflow is directed toward the volatile substance delivery structure.

* * * * *